(12) United States Patent
Guo et al.

(10) Patent No.: US 8,541,630 B2
(45) Date of Patent: Sep. 24, 2013

(54) PROCESS FOR PRODUCING DIMETHYL ETHER FROM METHANOL

(75) Inventors: Xiangbo Guo, Beijing (CN); Zheng Li, Beijing (CN); Qiang Li, Beijing (CN); Chaogang Xie, Beijing (CN); Keyong Yang, Beijing (CN); Anguo Mao, Beijing (CN); Xueliang Chang, Beijing (CN); Genquan Zhu, Beijing (CN)

(73) Assignees: China Petroleum & Chemical Corporation, Beijing (CN); Research Institute of Petroleum Processing, SINOPEC, Beijing (CN)

( * ) Notice: Subject to any disclaimer, the term of this patent is extended or adjusted under 35 U.S.C. 154(b) by 347 days.

(21) Appl. No.: 12/934,313

(22) PCT Filed: Mar. 26, 2008

(86) PCT No.: PCT/CN2008/000601
§ 371 (c)(1),
(2), (4) Date: Nov. 30, 2010

(87) PCT Pub. No.: WO2009/117851
PCT Pub. Date: Oct. 1, 2009

(65) Prior Publication Data
US 2011/0065963 A1    Mar. 17, 2011

(51) Int. Cl.
*C07C 41/09* (2006.01)
*C07C 43/04* (2006.01)
(52) U.S. Cl.
CPC .............. *C07C 41/09* (2013.01); *C07C 43/04* (2013.01)
USPC ........................................................ 568/698

(58) Field of Classification Search
None
See application file for complete search history.

(56) References Cited

U.S. PATENT DOCUMENTS

| | | | |
|---|---|---|---|
| 3,702,886 | A | 11/1972 | Argauer et al. |
| 4,425,256 | A | 1/1984 | Pilipski |
| 4,560,807 | A | 12/1985 | Murai et al. |
| 5,037,511 | A | 8/1991 | Dornhagen et al. |
| 5,043,517 | A | 8/1991 | Haddad |
| 5,354,345 | A | 10/1994 | Nehls, Jr. |
| 5,750,799 | A | 5/1998 | Van Dijk |
| 2004/0034255 | A1 | 2/2004 | Shoji et al. |
| 2004/0152583 | A1 | 8/2004 | Grosch et al. |
| 2010/0240932 | A1 | 9/2010 | Park et al. |

FOREIGN PATENT DOCUMENTS

| | | |
|---|---|---|
| CN | 95113028.5 A | 6/1996 |
| CN | 1153080 A | 7/1997 |
| CN | 1180064 A | 4/1998 |
| CN | 1301686 A | 7/2001 |
| CN | 1368493 A | 9/2002 |
| CN | 1562927 A | 1/2005 |

(Continued)

OTHER PUBLICATIONS

Weiguo, C. et al., "Applications and Development of DME" *Urban Gas* (2006) pp. 3-14, vol. 375(5), together with partial English translation.

*Primary Examiner* — Rosalynd Keys
(74) *Attorney, Agent, or Firm* — Scully, Scott, Murphy & Presser, P.C.

(57) ABSTRACT

Disclosed is a process for producing dimethyl ether from methanol, which is characterized in that the absorbing liquid used in said absorbing column is the bottom liquid of DME-fractionating column and/or bottom waste water of the methanol-recovering column. Said process can significantly reduce energy consumption of the apparatus.

25 Claims, 4 Drawing Sheets

(56) References Cited

FOREIGN PATENT DOCUMENTS

| | | | |
|---|---|---|---|
| CN | 1830934 A | | 9/2006 |
| CN | 1919819 A | | 2/2007 |
| CN | 101125802 A | | 2/2008 |
| CN | 101125802 A | * | 2/2008 |
| DE | 10 2006 038983 A1 | | 2/2008 |
| EP | 1 857 532 A | | 11/2007 |
| JP | 2004161673 | | 6/2004 |
| JP | 2008029988 | | 2/2008 |
| RU | 2 277 528 C1 | | 6/2006 |

* cited by examiner

PROCESS FOR PRODUCING DIMETHYL ETHER FROM METHANOL

TECHNICAL FIELD

The present invention relates to a method for producing dimethyl ether from methanol, and more particular, to a method for producing dimethyl ether by dehydrating methanol in gas phase in a reactor having a fluidizable, movable or flowable catalyst.

BACKGROUND

Dimethyl ether (DME) can be produced by one-step method and two-step method. The one-step method refers to one-step synthesis of DME from syngas, and the two-step method refers to synthesis of methanol from syngas, and then preparation of DME via dehydration.

The two-step method is carried out via two steps, i.e. synthesizing methanol from syngas, and then dehydrating methanol with the catalysis of an acid to prepare DME. The two-step method for the DME synthesis is a main process for producing DME home and abroad. Said two-step method uses fine methanol as feedstock, and has the advantages of less by-products of the dehydration reaction, high purity of dimethyl ether, mature technique, wide adaptability of the device, and simple post-treatment. Said two-step method can be directly used in a methanol factory, or other non-methanol factory having established public utilities. Generally, ZSM-5 molecular sieve comprising $\gamma Al_2O_3/SiO_2$ is used home and abroad as the dehydration catalyst. The dehydration temperature is controlled at 280-340° C. under a pressure of 0.5-0.8 MPa. The single-pass conversion of methanol is from 70 to 85%; and the DME selectivity is higher than 98%.

CN1180064A discloses a method of producing DME. Said method uses methanol as feedstock. The dehydration reaction is conducted at a relative low temperature (100-125° C.) under a normal pressure (0-0.05 MPa, gauge) in the presence of a fresh catalyst to produce a DME gas.

CN1368493A discloses a method of producing DME by methanol catalytic dehydration. It relates to a method of producing DME by a methanol catalytic dehydration, wherein said dehydration is conducted in the presence of a solid acid catalyst containing $SO_4^{2+}$. The $SO_4^{2+}$ content in the catalyst is preferably 2-25 wt %. The preferred catalyst support is selected from $\gamma$-$Al_2O_3$, $\eta$-$Al_2O_3$ and $SiO_2$.

CN1301686A discloses a method of producing DME by methanol dehydration. In said method, a catalyst, which uses kaolin as staring material and is modified with sulfuric acid, is used in the methanol dehydration to produce DME.

US2004/0034255A1 discloses a method of producing DME by catalyzing the gas phase methanol dehydration with an active alumina. Said active alumina has a pore diameter of 2.5-8.0 nm, wherein the $Na_2O$ content is below 0.07%.

The above mentioned methods primarily concern producing DME by catalyzing the methanol dehydration with composite solid acids, acid-modified kaolin, active alumina, and the like. Moreover, these methods mainly use fixed bed reactors to produce DME for fine chemicals and have a small production scale and a higher production cost.

In addition, the methanol dehydration is a strong exothermal reaction, and an adiabatic or continuously-heat-exchanging fixed bed reactor is generally used as the reactor, therefore, it is difficult to control the fixed bed temperature.

At present, the technical process of the catalytic dehydration of methanol in a gas phase to produce DME is generally as follows: the methanol feedstock is heated via a vaporizer or a vaporizing column and all vaporized, and then is sent to a reactor to conduct the reaction; the reaction product from the reactor is condensed, and then sent to a DME rectification column to conduct the rectifying separation; the DME product is obtained from the DME rectification column top, and a mixture of methanol and water is discharged from the DME rectification column bottom and enters a methanol recovery column to conduct the rectifying separation; methanol obtained from the methanol recovery column top is sent back to a methanol buffer tank to mix with the methanol feedstock and re-vaporize; and waste water from the methanol recovery column bottom is discharged out of the system.

U.S. Pat. No. 5,037,511 discloses a method of producing pure DME from methanol. In said method, methanol is vaporized by heat-exchange, and is subjected to the catalytic dehydration reaction in an adiabatic fixed bed reactor. The dehydrated reaction product enters a DME rectification column to conduct the rectification to produce a DME product of high purity. Noncondensable gas from the column top is washed with the methanol feedstock and then emitted. Due to the absence of heat collector in the reactor, the methanol dehydration reaction has a wide reaction temperature and a low methanol conversion, and produces more by-products. The rectification column is provided with a base-washing line and a water-washing line. The process is quite complex.

Chinese Patent ZL 95113028.5 discloses a method of producing DME from methanol. Its object is to provide a DME production process which can use a raw methanol as feedstock. The methanol feedstock has a concentration of 72% or more. The raw methanol feedstock is firstly sent to a vaporization-separation column to remove high boiling point materials and impurity, and then subjected to the catalytic dehydration reaction in the presence of a complex solid acid catalyst in a multistage-quenching-type reactor. Because methanol vapor enters the multistage-quenching-type reactor by stages, the gas which is subjected to the dehydration reaction in the former stage has a higher temperature and can be cooled by the methanol vapor with a lower temperature from the latter stage, so as to avoid the temperature rise and is in favor of increasing the conversion. However, since the methanol vapor has a low heat capacity, the methanol vapor has a limited function as the cooling medium. The reaction temperature is relatively high in the quenching-type reactor. The reaction temperature range is still relative wide so as to produce more by-products. Therefore, said method has a low single-pass conversion and a decreased product yield, and is not suitable for a large scale industrial production. The dehydrated product enters a packed DME rectification column to conduct the rectification so that a DME product with a purity of 90-99.99% can be produced. Noncondensable gas from the DME rectification column top enters the absorbing column to be washed. Noncondensable gas such as $H_2$ and $CH_4$ is emitted from the absorbing column top. The absorbing liquid used in the absorbing column is not described in details.

For the purpose of decreasing the massive energy consumption required by vaporizing the methanol feedstock and saving the device investment, Chinese patent 200410022020.5 proposes another method for producing DME. In said method, a methanol feedstock vaporizing column and a methanol recovery column are combined into a vaporizing-stripping column. The methanol feedstock with a methanol content of 70-99.99% enters the top of the vaporizing-stripping column to be vaporized in said column. The DME rectification column bottom liquid enters the middle part of the vaporizing-stripping column to separate methanol and water in said column. Said vaporizing-stripping column has both a function of vaporizing the methanol feedstock and a function of separating and recovering the aqueous methanol solution. It can not only dispense with the investment for the methanol recovery column and the auxiliary equipments, but also sharply reduce the energy consumption for recovering methanol from the mixed liquid from the DME rectification column bottom. However, in said method, all of the methanol feedstock enters the vaporizing column, the liquid phase load is too heavy, and it is difficult for the practical operation to guarantee the methanol concentration in the column bottom waste water to be reduced to a low level. Therefore, another stripping column is generally required to treat the waste water containing a little methanol coming from the vaporizing-stripping column. At the same time, due to the heavy liquid phase load, the vaporizing-stripping column should be provided with a large column diameter, and the investment consequently increases. Especially in case of a low concentration of the methanol feedstock, the concentration of the gas-phase methanol in the column top can not be adjusted, and it contains a large quantity of water; therefore, the reaction equilibrium conversion decreases so as to reduce the single-pass yield of the product.

In order to overcome the shortcoming of the heavy load on the vaporizing-stripping column of Chinese Patent ZL 200410022020.5, CN1919819A discloses a novel DME production process, wherein a part of the methanol material enters the methanol rectification recovery column top as a reflux liquid of the methanol rectification recovery column, and the other part enters the methanol pre-heater to heat-exchange with a gas mixture formed via reaction, enters the methanol superheater together with the methanol rectification recovery column top gas, and then enters the cooling-tube reactor to react. Said process can flexibly adjust the methanol vaporization depending on the different methanol feedstock, and reduce the heat load on the methanol rectification recovery column. However, since said process still adopts an adiabatic fixed bed reactor, the reaction temperature is relative high and more by-products are produced.

CN1830934A discloses a method for producing DME from methanol. Said method uses a fixed bed reactor having a built-in heat exchanging calandria. A methanol gas is used to remove a portion of reaction heat in the heat exchanging calandria. This solves the problem of a relative high reaction temperature in the fixed bed reactor to some extent. The methanol feedstock firstly enters an alcohol washing column to wash off the noncondensable tail gas coming from the DME rectification column as the reaction by-product, and then enters a methanol column to vaporize. The vaporized methanol enters the built-in heat exchanging calandria of the reactor to be superheated, and then enters the catalyst bed from the reactor top to react. The reaction product, after heat-exchanging, enters the DME rectification column in a gas phase to conduct the rectification. Said method utilizes a part of reaction heat, decreases the reaction temperature rise and reduces the reaction by-product. However, because the heat-collecting medium is the gas phase methanol, the removal of heat only by the sensible heat of the gas has a limited effect. Thus, the effect of controlling the reactor temperature and the energy consumption reduction are not remarkable.

In summary, one feature of the existing DME production methods lies in the methanol feedstock, including the methanol recovered by the methanol recovery column. The heat for its vaporization is always from the vaporizer, the vaporizing column, the methanol recovery column or the reaction product, and not directly from the methanol dehydration reaction. Therefore, the reaction has a high temperature rise and produces more by-products. On the other hand, in order to control the methanol dehydration reaction temperature in the reactor, the existing methods use the gas phase methanol as cooling medium, in a direct heat-exchanging manner for example in which the methanol gas is injected into the quenching-type reactor, or in an indirect heat-exchanging manner such as that of the built-in heat exchanging calandria. However, because the heat-collecting medium is the gas phase methanol, the removal of heat only by the sensible heat of the gas has a limited effect. Thus, the effect of controlling the reactor temperature and the energy consumption reduction are not remarkable.

Another feature of the existing DME production methods lies in that the methanol feedstock is used as the washing liquid or the absorbing liquid in the alcohol washing column or the absorbing column Noncondensable gases emitted from the top of the gas-liquid separator or the top of the DME rectification column entrain a small amount of methanol and DME, which are absorbed with the methanol feedstock in the existing methods. However, the solubility of DME in methanol is low, and therefore a large quantity of the methanol feedstock is required to be sent to the alcohol washing column or the absorbing column, and the absorbing efficiency is low. When the DME production is scaled up, methanol and DME entrained in a large quantity of noncondensable gases in the reaction product require a large quantity of methanol for washing and absorbing. This results in a heavy liquid phase load on the alcohol washing column and the absorbing column, a large column diameter, and an increased equipment investment.

SUMMARY

The purpose of the present invention is to provide a novel DME production process, which is a production process particularly suitable for producing DME with a fluidized bed reactor, may make full use of the reaction heat from the DME production by catalytically dehydrating methanol, reduces the methanol content in the noncondensable gas to be emitted, and can satisfy the demand on the large scale industrial DME production.

The present invention provides a method of producing dimethyl ether from methanol, which comprises the following steps of:

a methanol feedstock is sent to a catalyst-fluidizable reactor and contacted with the catalyst to conduct a dehydration reaction to produce a dehydrated reaction stream; and said dehydrated reaction stream is passed to a gas-solid separator to separate from the catalyst and obtain a carbon-deposited catalyst and a dehydrated reaction product, wherein, a portion or all of said carbon-deposited catalyst is sent to a regenerator to burn the coke for regeneration in a continuous or intermittent manner; and a regenerated catalyst is sent back to the reactor and contacted with the methanol feedstock to react, wherein, said dehydrated reaction product is sent to a separation device comprising an absorbing column and a DME rectification column, and optionally a methanol recovery column; a product stream consisting mainly of DME is obtained in the upper part of the DME rectification column; a noncondensable gas entrained with DME and/or methanol is obtained on the top of the DME rectification column; said noncondensable gas is sent to the absorbing column to absorb the entrained DME and/or methanol with an absorbing liquid; the DME rectification column bottom liquid consists substantially of unconverted methanol and water; the DME rectification column bottom liquid is optionally separated by the methanol recovery column to obtain methanol in the upper part of the methanol recovery column and waste water at the methanol recovery column bottom, and wherein the absorbing liquid used in the absorbing column is the DME rectification column bottom liquid and/or waste water from the methanol recovery column bottom.

The method of the present invention can efficiently control a bed reaction temperature, and guarantee a continuous conversion of methanol into DME. The methanol conversion is generally above 80%. The DME selectivity is higher than 98%. The energy consumption can be remarkably reduced.

The methanol feedstock of the present invention has a methanol content of 5-100 wt %, preferably 50-100 wt %, more preferably 90-100 wt %, and can contain a small quantity of impurity such as water. The methanol feedstock is a raw methanol produced by gasification and synthesization starting from a variety of fossil-fuels such as natural gas, coal, oil sand and petroleum and or a methanol from any other source. The methanol feedstock can be fed in a liquid phase, or in a gas phase after the heat exchange with the reaction product or other heat sources.

The catalyst may contain Y-zeolite and optionally other molecular sieve but not contain inorganic oxide(s) and clay, wherein the weight ratio of other molecular sieve to Y-zeolite is 0-10. Said catalyst preferably contains inorganic oxide(s), clay, Y-zeolite, and optionally other molecular sieve, wherein the weight ratio of other molecular sieve to Y-zeolite is 0-10, and a total of other molecular sieve and Y-zeolite comprises 10-80 wt % of the catalyst.

Said Y-zeolite includes Y-type zeolite and their derivatives or modified zeolites, and is selected from the group consisting of Y, HY, REY, REHY, USY, REUSY and mixtures thereof.

Said other molecular sieve is one or more selected from meso porous zeolites, Beta-zeolites, and SAPO-molecular sieves.

Said meso porous zeolite includes ZRP series (rare earth-modified), ZSP series (iron-modified), ZSM series zeolites and their derivative or modified zeolites. For the more detailed description of ZRP, a reference may be made to U.S. Pat. No. 5,232,675. Said ZSM series zeolite is selected from the group consisting of ZSM-5, ZSM-11, ZSM-12, ZSM-22, ZSM-23, ZSM-35, ZSM38, ZSM-48, and other zeolites having a similar structure. For more detailed description of ZSM-5, a reference may be made to U.S. Pat. No. 3,702,886.

A more preferred catalyst contains Y-zeolites, meso porous zeolites, inorganic oxides, and clay, wherein the weight ratio of the meso porous zeolite to the Y-zeolite is 0.1-10, and the total weight of the meso porous zeolite and the Y-zeolite accounts for 10-80% of total weight of the catalyst. Said inorganic oxide is selected from the group consisting of alumina, silica, amorphous silica-alumina and mixtures thereof. The clay is kaolin and/or halloysite.

The dehydration reaction is conducted at a temperature of 100-550° C., and preferably 150-380° C., under a pressure (pressures in the present description are all expressed as the gauge pressure) of 1~1500 kPa, preferably 1~1000 kPa, and more preferably 1~900 kPa, with a weight ratio of the catalyst to the methanol feedstock of 0.001-50, preferably 0.005~40, at a weight hourly space velocity of 0.01-100 h$^{-1}$, preferably 0.1-50 h$^{-1}$.

The proportion of the carbon-deposited catalyst subjected to coke-burning is 0.5-100% by the total weight of the carbon-deposited catalyst. When a portion of the carbon-deposited catalyst enters the regenerator for the coke-burning regeneration, the remaining carbon-deposited catalyst returns to the reactor, and said portion of the carbon-deposited catalyst subjected to coke-burning comprises 0.5-99% by the total weight of the carbon-deposited catalyst.

The regeneration is one-stage regeneration or two-stage regeneration, and said regenerated catalyst is a partially regenerated catalyst (i.e. half-regenerated catalyst) and/or a full regenerated catalyst.

Said catalyst containing Y-zeolite is selected from the group consisting of a fresh catalyst, a regenerated catalyst, a half-regenerated catalyst, a catalyst to be regenerated, and a combination thereof.

The catalyst-fluidizable reactor is selected from the group consisting of a fluidized bed, a riser, a descending transfer line reactor, a composite reactor of riser and fluidized bed, a composite reactor of riser and descending transfer line, a composite reactor of two or more risers, a composite reactor of two or more fluidized beds, and a composite reactor of two or more descending transfer lines. Each of the above reactors may be divided into two or more reaction zones. Preferably, said riser is one or more selected from an iso-diameter riser, an equal-velocity riser, and various variable-diameter risers. Preferably, said fluidized bed is one or more selected from a fixed fluidized bed, a particulate fluidization bed, a bubbling bed, a turbulent bed, a quick bed, a transfer bed, and a dense-phase fluidized bed. The preferable reactor is a fluidized bed, more preferably a dense-phase fluidized bed.

The regenerated catalyst may be not cooled or may be cooled to 100-650° C., and then sent back to the reactor. The cooling can be conducted in a direct or indirect heat-exchange manner. The direct heat-exchange is to directly contact the regenerated catalyst with air or steam having a lower temperature for heat-exchange. This air is a part or all of the air sent to the regenerator after compressing with an air compressor. That is to say, the high temperature heat energy from a portion of the regenerated catalyst is utilized to pre-heat the air coming into the regenerator. The direct heat-exchanger is embodied in a fluidized bed or a riser. The cooled catalyst, after separating in a cyclone separator, is stripped with hot steam to remove impurity gas such as $N_2$, $O_2$, and $CO_2$, and then sent into a catalytic conversion reactor of alcohols. The indirect heat-exchange is to use a heat exchanger, through the shell of which the hot catalyst passes and through the tube of which the saturated water or other heat-exchanging medium passes.

According to one preferred embodiment, the methanol feedstock is indirectly heat-exchanged with the reaction stream and the catalyst in the reactor and/or the catalyst in the regenerator before being fed to the catalyst-fluidizable reactor and contacted with the catalyst.

According to one preferred embodiment, the separation device comprises an absorbing column, a DME rectification column, and a methanol recovery column, wherein 99.9-90 vol % of the DME rectification column bottom liquid is sent into the methanol recovery column, and 0.1-10 vol % of the DME rectification column bottom liquid is sent into the absorbing column as the absorbing liquid.

According to one preferred embodiment, the separation device further comprises a gas-liquid separator, wherein the dehydrated reaction product and/or the absorbing column bottom liquid is sent to the gas-liquid separator; after the gas-liquid separation, a liquid phase portion and a gas phase portion are obtained, wherein the liquid phase portion is sent to the DME rectification column, and the gas phase portion is sent to the absorbing column.

According to one preferred embodiment, the DME rectification column is a packed column or a plate column. It is operated under a pressure of 0.1-1.5 MPa, preferably 0.5-1.2 MPa. It is operated at a column top temperature of 20-90° C. and a column bottom temperature of 100-220° C. It has a theoretical plate number of 10-35. The inlet is at a position between the 4th plate and the 16th plate counted from the column top. The outlet for DME is at a position between the 1st plate and the 5th plate counted from the column top.

According to one preferred embodiment, the methanol recovery column is a packed column or a plate column. It is operated under a pressure of 0.01-0.6 MPa, preferably 0.1-0.5 MPa. It is operated at a column top temperature of 65-170° C. and a bottom column temperature of 100-220° C. It has a theoretical plate number of 10-35. The inlet is at a position between the 4th plate and the 16th plate counted from the column top. The outlet for methanol vapor is at a position between the 1st plate and the 5th plate counted from the column top.

According to one preferred embodiment, the absorbing/recovery column is a packed column or a plate column. It is operated under a pressure of 0.1-1.5 MPa, preferably 0.5-1.2 MPa. It is operated at a temperature of 30-70° C. It has a theoretical plate number of 1-15. The inlet is in the middle-lower part of the column.

THE DESCRIPTION OF DRAWINGS

PREFERRED EMBODIMENTS OF THE INVENTION

The following detailed description of preferred embodiments of the invention will be made in reference to the accompanying drawings. The provided examples are merely illustrative and are not to be taken as limitations upon the scope of the invention, which is defined solely by the appended claims and their equivalents. Various changes and modifications to the disclosed embodiments will be apparent to those skilled in the art and can be made without departing from the spirit and scope thereof.

Figure 1:
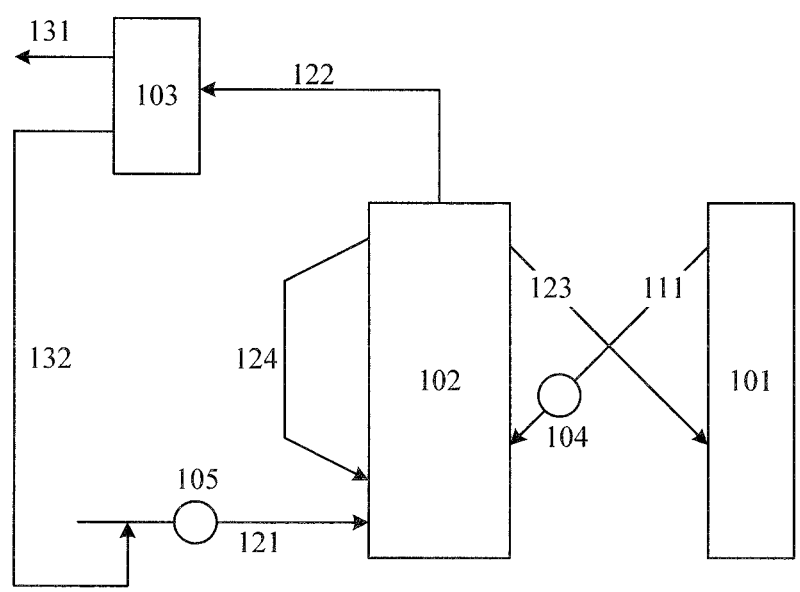
FIG. 1 is a brief process chart of producing DME from methanol according to the present invention.

A brief process chart of the present invention is shown in FIG. 1, wherein a regenerator is shown at 101 and a methanol dehydration reactor is shown at 102.

A hot catalyst from the regenerator 101 is sent via a line 111 to a reactor 102. Before entering the reactor 102, the hot catalyst is cooled in a heat-exchanger 104. A methanol feedstock, after heat exchanging in a heat-exchanger 105, is sent via a line 121 to the reactor 102, and is contacted with the hot catalyst from the line 111 to conduct a methanol dehydration reaction. After the reaction is complete, a formed reaction product consisting mainly of DME is separated from the catalyst, leaves the reactor 102 via a line 122, and is sent to a separation device 103. In the separation device, the reaction product is further separated into a gas product consisting mainly of DME and a liquid product consisting mainly of methanol. The gas product leaves the device via a line 131 and is sent to a tank farm (not shown). The separated liquid methanol is sent back via a line 132 to a feedstock system (not shown) for recycle use. A portion of the separated catalyst is sent back via a line 124 to the methanol dehydration reactor 102 for use, and another portion is sent back via a line 123 to the regenerator for repeated use after regeneration.

Figure 2:
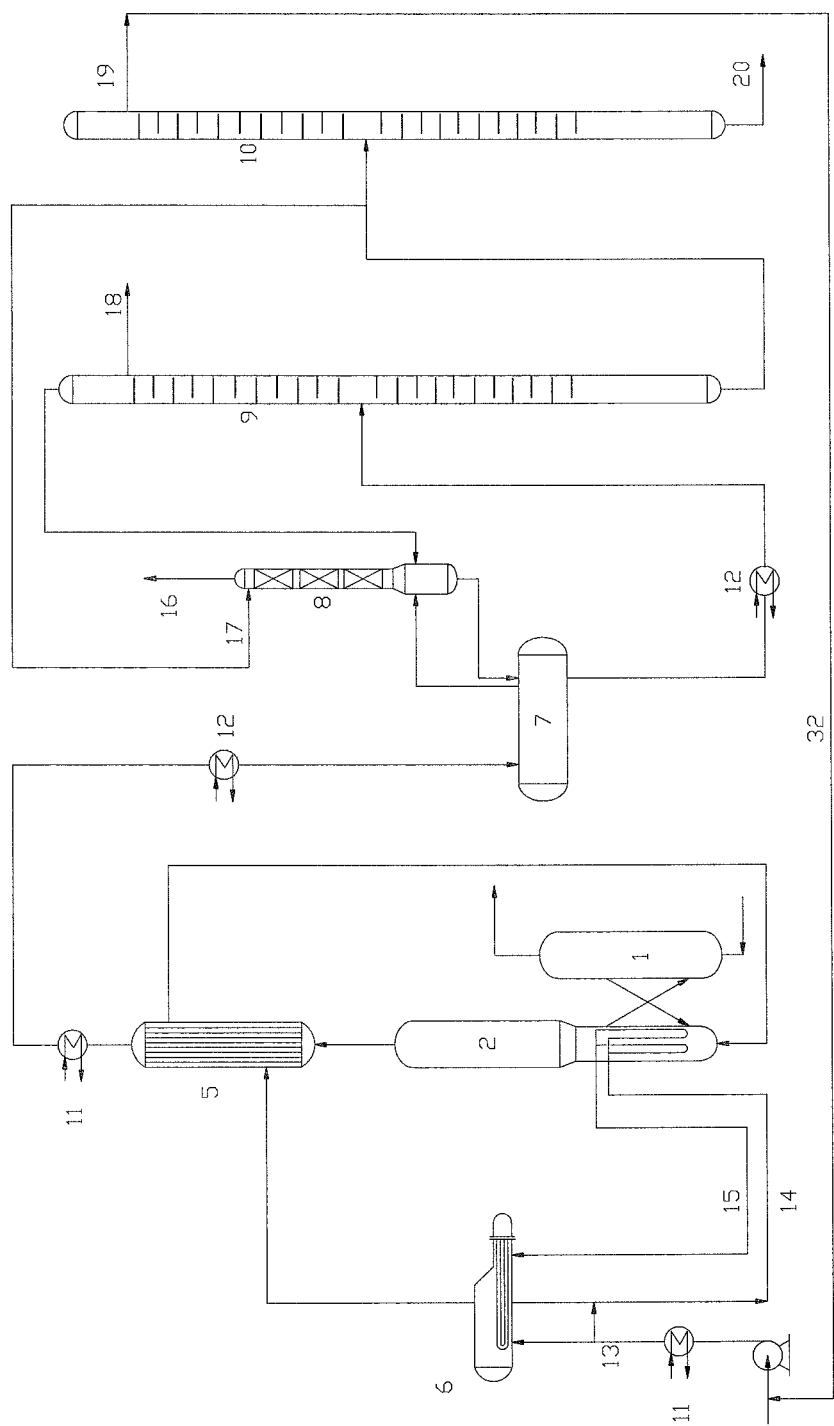
FIG. 2 is a detailed process chart according to one embodiment of the present invention.
Figure 3:
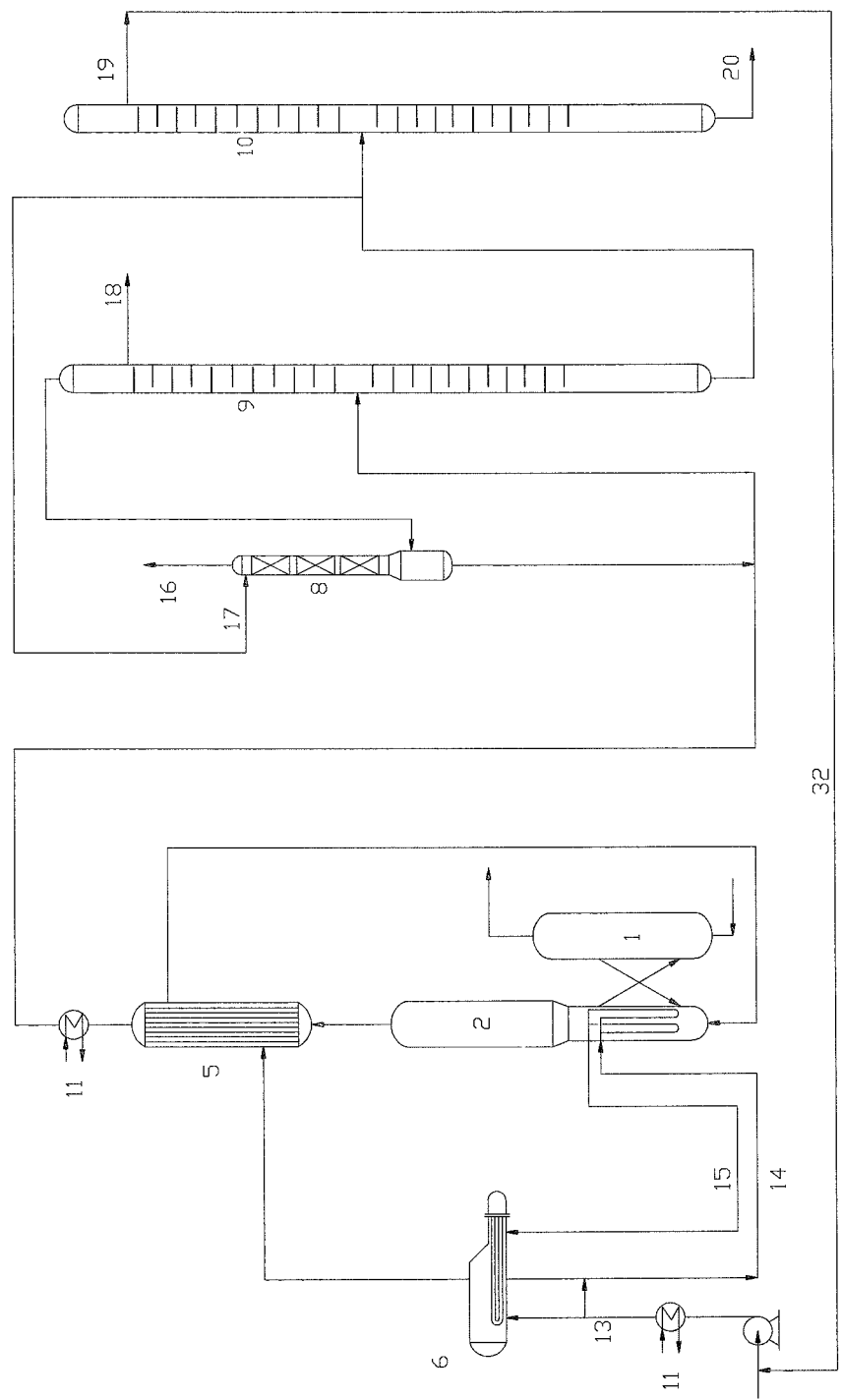
FIG. 3 is a detailed process chart according to one embodiment of the present invention.

The process of the present invention will be further illustrated in reference to FIGS. 2 and 3, but is not limit thereto.

As shown in FIG. 2, a methanol feedstock having a methanol concentration of 70-99.99% by weight is sent to a methanol pre-heater 11 to heat exchange with a formed reaction mixture, and then to a methanol vaporizer 6 for vaporization. The methanol vaporizer has a structure of horizontal type or vertical type, and is operated under a pressure of 0.1-1.5 MPa at a temperature of 65-160° C. There are a saturated methanol vapor in the upper part of the methanol vaporizer and a saturated methanol liquid in the lower part of the methanol vaporizer. A methanol gas coming from the top of the vaporizer 6 passes through a methanol superheating heat-exchanger 5 to be heated to a temperature of 130-240° C., preferably 180-220° C., and enters a fluidized bed reactor 2 from the bottom to conduct a catalytic dehydration reaction. A catalyst in the reactor 2, after deactivation, is sent to a regenerator 1 to regenerate under a pressure of 0.1-1.5 MPa, at a space velocity of 0.1-10 $h^{-1}$, at a regeneration temperature of 450-750° C., and preferably 550-700° C. Depending on the deactivation rate of the catalyst in the reactor, a part of or all of the catalyst may be regenerated in a continuous or intermittent manner. A reaction product is collected from the top of the reactor 2, passes through the methanol superheating heat-exchanger 5, the methanol pre-heater 11 and a raw DME pre-heater 12, and enters a gas-liquid separator 7. After the gas-liquid separation, a liquid fraction enters the middle of a DME rectification column 9, and a gas fraction enters an absorbing column 8 methanol, DME and the like entrained in a reaction noncondensable gas is absorbed by an absorbing liquid 17 in the absorbing column and returns to the gas-liquid separator 7. A lighter component 16 such as $H_2$ and $CH_4$ is emitted from the top of the absorbing column 8. The liquid reaction product entering the DME rectification column 9 is separated by rectification to collect a qualified DME product 18 in the upper part of the rectification column, and the noncondensable gas obtained on the top of the rectification column is sent to the absorbing column 8. A column bottom liquid of the column 9 is mainly composed of the unconverted methanol and the water produced in the reaction (including the water contained in the feedstock). Most of, for example, 99.9-90%, preferably 99%-92%, more preferably 99%-95% of the column bottom liquid is sent to a methanol recovery column 10 to recover methanol. A small portion of, for example, 0.1%-10%, preferably 1%-8%, more preferably 1%-5% of the column bottom liquid returns to the absorbing column 8 as the absorbing liquid 17. A methanol stream 19 is collected in the upper part of the methanol recovery column 10 and returns to a feedstock system (not shown). Waste water 20 of the column bottom liquid is sent to a waste water treatment system (not shown).

When the DME production is scaled up, in order to save the equipment investment and reduce the load of the DME rectification column, a process scheme of the present invention as shown in FIG. 3 can be used: the reaction product is collected from the top of the reactor 2, passes through the methanol superheating heat-exchanger 5 and the methanol pre-heater 11, enters the middle of the DME rectification column 9 in a saturated gas-liquid two-phase form, and is separated by rectification to collect a qualified DME product 18 in the upper part of the rectification column. The noncondensable gas obtained on the top of the rectification column is sent to the absorbing column 8. methanol, DME and the like entrained in the top noncondensable gas is absorbed by the absorbing liquid 17 in the absorbing column 8 and returns to the middle of the DME rectification column 9. A lighter component 16 such as $H_2$ and $CH_4$ is emitted from the top of the absorbing column 8.

The methanol dehydration reaction is a strong exothermic reaction. The temperature rise is adverse for increasing the equilibrium conversion of the dehydration reaction. For molecular sieve catalysts, the reaction should be conducted at a temperature of 240-350° C. so as to have a relative high reaction velocity and stability. If the temperature is too high, more by-products will be produced. This will reduce the reaction selectivity. Therefore, once a suitable reaction temperature is reached, it is necessary to draw out the reaction heat, control the temperature rise in the catalyst bed and maintain the temperature uniformity in the catalyst bed so as to guarantee a high reaction conversion and a high selectivity. The movement of the fluid and the catalyst particles in the fluidized bed reactor according to the present invention imparts a good heat-transfer property to the catalyst bed. The temperature inside the bed is uniform and easy to control. Therefore, said fluidized bed reactor is in particular suitable for the strong exothermal reaction such as the methanol catalytic dehydration reaction. The fluidized bed reactor can be provided with an interior heat collector of coil tube type or U-tube type, or an exterior heat collector. The heat-collecting medium can be a saturated methanol liquid coming from the methanol vaporizer 6 and/or a heat-exchanged or not-heat-exchanged unsaturated cold methanol liquid coming from a methanol pump. The saturated methanol liquid and/or the unsaturated cold methanol liquid, after vaporizing in the interior heat collector or the exterior heat collector to remove heat, returns to the methanol vaporizer. Along with the reaction, the temperature in the catalyst bed gradually rises, and the resulting heat is removed by the methanol liquid in the interior heat collector or the exterior heat collector so that the temperature rise is effectively controlled, the reaction temperature is stabilized at an optimal reaction temperature range, and the side-reaction is effectively avoid. The vaporization of methanol in the heat collector directly utilizes the reaction heat. After separating the methanol gas-liquid mixture returning to the methanol vaporizer 6, the methanol vapor is sent as feedstock for the reaction and the saturated liquid can collect heat circularly. This is an ingenious design of removing the heat with the methanol liquid according to the present invention. Said method reduces the energy consumption of the methanol vaporizer and utilizes thoroughly the reaction heat so as to achieve the object of controlling the temperature. Furthermore, the saturated methanol liquid coming from the methanol vaporizer and/or the heat-exchanged or not-heat-exchanged unsaturated cold methanol liquid coming from the methanol pump may be also used as the heat-collecting medium of the regenerator. Utilization of the heat from the coke-burning of the catalyst in the regenerator can further decrease the heat load on the methanol vaporizer. However, since there is a safety risk of utilizing methanol as the heat-collecting medium in the regenerator, it needs an additional detailed design if practiced.

As mentioned above, using the methanol vaporizer according to the present invention, which has both a function of vaporizing the methanol feedstock and a capability of collecting the heat directly from the reactor and/or the regenerator, not only dispenses with the saturated steam drum required for collecting heat from the reactor and/or the regenerator with saturated water, but also can reduce the energy consumption of vaporizing the methanol sharply by removing the reaction heat or the coke-burning heat with the methanol vaporization.

The DME rectification column is a packed column or a plate column. It is operated under a pressure of 0.1-1.5 MPa, preferably 0.5-1.2 MPa. It is operated at a column top temperature of 20-90° C. and a column bottom temperature of 100-220° C. It has a theoretical plate number of 10-35. The inlet is at a position between the $4^{th}$ plate and the $16^{th}$ plate counted from the column top. The outlet for DME is at a position between the $1^{st}$ plate and the $5^{th}$ plate counted from the column top. The produced DME may have a purity of 90-99.99%. The DME rectification column may be provided with a condenser at the column top. After condensation, one part refluxes, and the other leaves the column as product. The column top mass reflux ratio is (0.1-5):1. A small amount of DME and other hydrocarbon components are sent from the column top to the absorbing column.

The methanol recovery column is a packed column or a plate column. It is operated under a pressure of 0.01-0.6 MPa, preferably 0.1-0.5 MPa. It is operated at a column top temperature of 65-170° C. and a bottom column temperature of 100-220° C. The methanol concentration is below 100 ppm at the column bottom. The methanol recovery column has a theoretical plate number of 10-35. The inlet is at a position between the $4^{th}$ plate and the $16^{th}$ plate counted from the column top. The outlet for methanol vapor is at a position between the $1^{st}$ plate and the $5^{th}$ plate counted from the column top. The methanol recovery column may be provided with a condenser at the column top. After condensation, one part refluxes, and the other leaves the column as product. The column top mass reflux ratio is (0.1-5):1.

The absorbing column is a packed column or a plate column. It is operated under a pressure of 0.1-1.5 MPa, preferably 0.5-1.2 MPa. It is operated at a temperature of 30-70° C. It has a theoretical plate number of 1-15. The inlet is in the middle-lower part of the column. The absorbing liquid is the cooled column bottom liquid of the DME rectification column and/or waste water from the methanol recovery column bottom. Cheng Weiguo and Hu Juan describe, in *Applications and development of DME*, URBAN GAS, 2006, 375 (5): 3-14, the liquid in which DME has a highest solubility is water, as shown in Table 1.

TABLE 1

The solubility of DME

| Solvent | Solubility (wt %) | Solvent | Solubility (wt %) |
|---|---|---|---|
| Water (24° C.) | 35.3 | CCl$_4$ (25° C.) | 16.33 |
| Gasoline | | Acetone (25° C.) | 11.83 |
| −40° C. | 64 | Benzene (25° C.) | 15.29 |
| 0° C. | 19 | Chlorobenzene (106 kPa, 25° C.) | 18.56 |
| 25° C. | 7 | Methyl acetate (93.86 kPa, 25° C.) | 11.1 |

Figure 4:
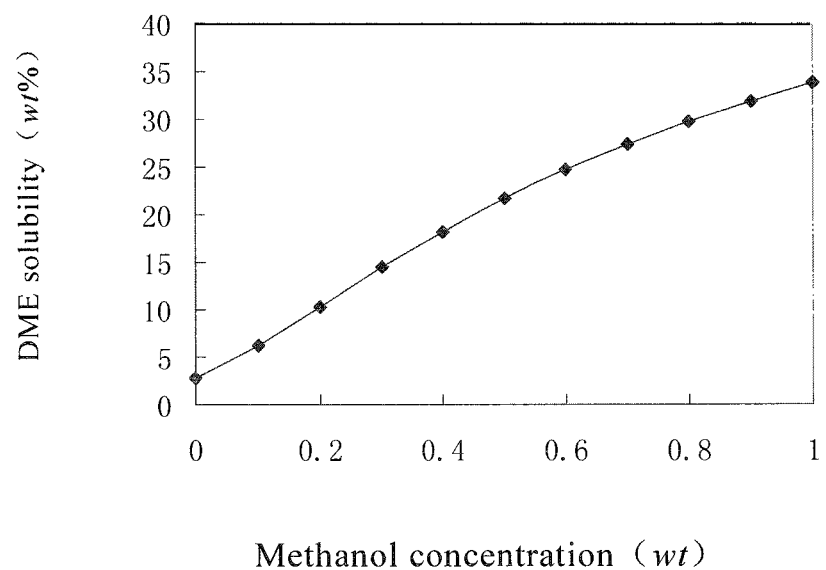
FIG. 4 is a chart showing the solubility of DME in an aqueous methanol solution at 25° C. under a normal pressure.

The column bottom liquid of the DME rectification column is a mixed liquid of methanol and water, and also has a high solubility for methanol and DME gases relative to the methanol feedstock of high purity. The solubility of DME in an aqueous methanol solution at 25° C. under a normal pressure is calculated at various methanol concentrations, and plotted in FIG. 4. It can be seen that comparing with using the methanol feedstock as the absorbing liquid, using the cooled column bottom liquid of the DME rectification column or waste water from the methanol recovery column bottom as the absorbing liquid for the alcohol washing column/the absorbing column, on the one hand, can reduce the feed amount of the absorbing liquid sharply, and on the other hand, can avoid the problem of entraining DME product and other impurity in the feedstock caused by using the methanol feedstock as the absorbing liquid.

With the method for producing DME from methanol according to the present invention, the reaction temperature in the bed can be effectively controlled so as to guarantee a continuous conversion of methanol into DME. In one embodiment of the present invention, the methanol conversion is 80% or more, and the DME selectivity is 98% or more. In another embodiment of the present invention, the methanol conversion is 85% or more, and the DME selectivity is 99% or more.

EXAMPLES

Examples 1-4 were conducted in a pilot fixed fluidized bed experimental apparatus, Examples 5-6 were conducted in an industrial experimental apparatus, and Examples 7-8 were based on the calculation results with a common chemical engineering ASPEN PLUS 12.1. All of the methanol reactors were fluidized bed reactors. The properties of the methanol feedstock used in the Examples (produced by Beijing Chemical Works) are shown in Table 2.

TABLE 2

| | |
|---|---|
| Methanol content, wt % | ≥99.5 |
| Density (20° C.), g/ml | 0.792 |
| Molecular weight | 32.04 |
| Boiling point | 64.5 |

Example 1

The catalyst used in this example has a designation of MTD-1 (containing 30 wt % of USY zeolite, 5 wt % of ZSM-5 zeolite, and the balance of support, all based on the total weight of catalyst).
A gaseous methanol feedstock was fed into the fluidized bed reactor to contact with the MTD-1 catalyst and react at a temperature of 280° C. under a pressure of 0.1 MPa (gauge) at a weight ratio of the catalyst to the methanol feedstock (catalyst/alcohol ratio) of 2.5 with a weight hourly space velocity (WHSV) of 3.0 $h^{-1}$. The reaction stream was separated to produce a carbon-deposited catalyst and a product stream. The product stream was further separated to obtain the target product of DME. The product distribution is shown in FIG. 3. The unreacted methanol was sent back to the fluidized bed reactor. The carbon-deposited catalyst was divided into two parts, 50 wt % of which was sent to a regenerator for the coke-burning regeneration, and the remaining 50 wt % of which was sent back to the fluidized bed reactor via an inner circulation.
50 wt % of the carbon-deposited catalyst was regenerated. Then the regenerated catalyst was cooled down to 180° C. and sent back to the fluidized bed for recycle use.

Example 2

The catalyst used in this example has a designation of MTD-2 (containing 35 wt % of USY zeolite, and the balance of support, all based on the total weight of catalyst).
A liquid methanol feedstock was fed into the fluidized bed reactor to contact with the MTD-2 catalyst and react at a temperature of 380° C. under a pressure of 0.1 MPa (gauge) at a weight ratio of the catalyst to the methanol feedstock (catalyst/alcohol ratio) of 40 with a weight hourly space velocity (WHSV) of 50 $h^{-1}$. The reaction stream was separated to produce a carbon-deposited catalyst and a product stream. The product stream was further separated to obtain the target product of DME. The product distribution is shown in FIG. 3. The excessive methanol was sent back to the fluidized bed reactor. All of the carbon-deposited catalyst was sent to a regenerator for the coke-burning regeneration.
All of the carbon-deposited catalyst was regenerated. Then the regenerated catalyst was cooled down to 410° C. and sent back to the fluidized bed for recycle use.

Example 3

The catalyst used in this example has a designation of MTD-3 (containing 30 wt % of USY zeolite, 5 wt % of Beta zeolite, and the balance of support, all based on the total weight of catalyst).
A liquid methanol feedstock was fed into the fluidized bed reactor to contact with the MTD-3 catalyst and react at a temperature of 150° C. under a pressure of 0.1 MPa (gauge) at a weight ratio of the catalyst to the methanol feedstock (catalyst/alcohol ratio) of 6 with a weight hourly space velocity (WHSV) of 0.1 $h^{-1}$. The reaction stream was separated to produce a carbon-deposited catalyst and a product stream. The product stream was further separated to obtain the target product of DME. The product distribution is shown in FIG. 3. The excessive methanol was sent back to the fluidized bed reactor. The carbon-deposited catalyst was divided into two parts, 25 wt % of which was sent to a regenerator for the coke-burning regeneration, and the remaining 75 wt % of which was sent back to the fluidized bed reactor via an inner circulation.
25 wt % of the carbon-deposited catalyst was regenerated. Then the regenerated catalyst was cooled down to 280° C. and sent back to the fluidized bed for recycle use.

Example 4

The catalyst used in this example has a designation of MTD-4 (containing 30 wt % of USY zeolite, 5 wt % of SAPO zeolite, and the balance of support, all based on the total weight of catalyst).
A liquid methanol feedstock was fed into the fluidized bed reactor to contact with the MTD-4 catalyst and react at a temperature of 250° C. under a pressure of 0.1 MPa (gauge) at a weight ratio of the catalyst to the methanol feedstock (catalyst/alcohol ratio) of 20 with a weight hourly space velocity (WHSV) of 10 $h^{-1}$. The reaction stream was separated to produce a carbon-deposited catalyst and a product stream. The product stream was further separated to obtain the target product of DME. The product distribution is shown in FIG. 3. The excessive methanol was sent back to the fluidized bed reactor. The carbon-deposited catalyst was divided into two parts, 50 wt % of which was sent to a regenerator for the coke-burning regeneration, and the remaining 50 wt % of which was sent back to the fluidized bed reactor via an inner circulation.
50 wt % of the carbon-deposited catalyst was regenerated. Then the regenerated catalyst was cooled down to 340° C. and sent back to the fluidized bed for recycle use.

TABLE 3

| | Examples | | | |
|---|---|---|---|---|
| | 1 | 2 | 3 | 4 |
| Active Component(s) in Catalyst | Y + ZSM-5 | Y | Y + Beta | Y + SAPO |
| Methanol Catalytic Conversion | | | | |
| Reaction Conditions | | | | |
| Temperature, ° C. | 280 | 380 | 150 | 250 |
| Pressure (gauge), MPa | 0.1 | 0.1 | 0.1 | 0.1 |
| Catalyst/alcohol ratio | 2.5 | 40 | 6 | 20 |
| WHSV, h$^{-1}$ | 3.0 | 50 | 0.1 | 10 |
| Product distribution, wt % | | | | |
| DME | 57.24 | 56.56 | 59.98 | 56.45 |
| Light hydrocarbons | 0.58 | 0.57 | 0.61 | 0.57 |
| Water | 24.31 | 23.65 | 24.96 | 23.59 |
| Coke | 0.85 | 0.56 | 0.51 | 0.55 |
| Unconverted methanol | 17.02 | 18.66 | 13.94 | 18.84 |
| Methanol conversion, % | 82.98 | 81.34 | 86.06 | 81.16 |
| DME selectivity, % | >98 | >98 | >98 | >98 |

Example 5

The process chart of the DME production process is shown in FIG. 2.

The DME production scale was 50,000 tons/year. The pressure in the fluidized bed reactor was 1.0 MPa (gauge). The methanol feedstock was an industrial methanol with a purity of 99%.

The methanol feedstock at 13 was fed at a feed rate of 10663 kg/h into the methanol vaporizer 6, wherein the fresh methanol was at 8783 kg/h and the recycled methanol was at 1880 kg/h. The methanol vaporizer 6 was operated at a temperature of 154° C. under a pressure of 1.5 MPa (gauge) with a heat supply of 2000 KW by a 1.15 MPa (gauge) steam. The saturated methanol vapor was collected from the top of the vaporizer, sent into the heat-exchanger 5 to be superheated to 209° C., and then sent to the fluidized bed reactor.

The saturated methanol liquid from the bottom of the methanol vaporizer 6 was sent to the heat-collecting tube of the interior heat collector or the exterior heat collector at a rate of 30000 kg/h to generate a 1.5 MPa methanol vapor at a rate of 3020 kg/h with the methanol vaporization latent heat. The methanol vapor and the saturated methanol liquid returned to the methanol vaporizer, and removed a methanol dehydration reaction heat of about 800 KW from the reactor. The reaction temperature could be controlled in a range of 260-280° C.

The methanol dehydration reaction product was obtained at the outlet of the fluidized bed reactor 2: 6308 kg/h of DME vapor, 1880 kg/h of methanol vapor, 2469 kg/h of steam and 6 kg/h of noncondensable gas. The reaction product having a temperature of 280° C. entered the heat-exchanger 5 to heat-exchange with the fed methanol vapor to reach a temperature of 230° C., then entered the methanol pre-heater 11 and the raw DME pre-heater 12 to further condense to a temperature of about 40° C., and then entered the gas-liquid separator 7 to conduct a gas-liquid separation at an operation pressure of 1.0 MPa (gauge) to obtain a liquid phase and a gas phase. The liquid phase was a raw DME liquid with a purity of about 55%. The gas phase included noncondensable gas such as H2, CO, CH4 and CO2, and saturated DME and methanol vapors. 24 kg/h of the gas phase material entered the absorbing column 8, and DME in the gas phase was absorbed with a 200 kg/h methanol-water mixed liquid from the DME rectification column bottom. The absorbed liquid was sent back to the gas-liquid separator 7. About 4 kg/h of the tail gas after absorption was depressurized and vented to a torch tower.

The liquid phase raw DME from the gas-liquid separator 7 was pumped into the DME rectification column 9 to rectify. The ratio of the top reflux quantity and the produced quantity at 18 was 1.1, and the DME product produced at 18 was at 6310 kg/h with a DME content of ≥99.9%. The noncondensable gas, and DME and methanol vapors from the DME column top returned at 32 kg/h to the absorbing column 8 to conduct the absorption. The reboiler of the DME rectification column 9 required 1.1 MPa (gauge) steam to supply a heat of 1500 KW.

The bottom liquid of the DME rectification column 9 was an aqueous methanol solution with a methanol content of about 40%, 200 kg/h of which was used as the absorbing liquid to the absorbing column 8, and the remaining 4349 kg/h of which was sent to the methanol recovery column 10. 1880 kg/h of the methanol material 19 (containing 2 kg/h of water) was recovered from the column top for recycle use. 2467 kg/h of the process waste water leaving the methanol recovery column, after cooling in a water-cooler, was sent to the waste water treatment system.

The DME rectification column was a plate column. It was operated under a pressure of 1.1 MPa at a column top temperature of 50° C. and a column bottom temperature of 158° C. It had a theoretical plate number of 25. The inlet was at the 14$^{th}$ plate counted from the column top. The outlet for DME was at the 1$^{st}$ plate counted from the column top. The DME rectification column was provided with a condenser at the column top. The column top mass reflux ratio was 1.1:1.

The methanol recovery column was a plate column. It was operated under a pressure of 0.2 MPa at a column top temperature of 75° C. and a bottom column temperature of 114° C. The methanol recovery column had a theoretical plate number of 25. The inlet was at the 14$^{th}$ plate counted from the column top. The outlet for methanol vapor was at the 1$^{st}$ plate counted from the column top. The methanol recovery column was provided with a condenser at the column top. The column top mass reflux ratio was 2:1.

The absorbing column was a packed column. It was operated under a pressure of 1.0 MPa. It was operated at a temperature of 40° C. It had a theoretical plate number of 6. The inlet was in the middle-lower part of the column.

Example 6

The process chart of the DME production process is shown in FIG. 2.

The DME production scale was 100,000 tons/year. The pressure in the fluidized bed reactor was 0.8 MPa (gauge). The methanol feedstock was an industrial methanol with a purity of 90%.

The methanol feedstock at 13 was at 23260 kg/h, wherein the fresh methanol was at 17567 kg/h, water was at 1933 kg/h and the recycled methanol was at 3760 kg/h. The methanol vaporizer 6 had a heat load of 5705 KW and was operated at a temperature of 158° C. under a pressure of 1.5 MPa (gauge). The methanol vapor was sent to the heat-exchanger 5 to be superheated to 200° C. and then to the fluidized bed reactor.

The saturated methanol liquid from the bottom of the methanol vaporizer 6 was sent to the heat-collecting tube of the interior heat collector or the exterior heat collector at a rate of 50000 kg/h to generate a 1.5 MPa methanol vapor at a rate of 4500 kg/h with the methanol vaporization latent heat. The methanol vapor and the saturated methanol liquid returned to the methanol vaporizer, and removed a methanol dehydration reaction heat of about 1200 KW from the reactor. The reaction temperature could be controlled in a range of 250-280° C.

The methanol dehydration reaction product was obtained at the outlet of the fluidized bed reactor 2: 12618 kg/h of DME vapor, 3760 kg/h of methanol vapor, 6871 kg/h of steam and 11 kg/h of noncondensable gas. The reaction product having a temperature of 280° C. entered the heat-exchanger 5 to heat-exchange with the fed methanol vapor to reach a temperature of 240° C., then entered the methanol pre-heater 11 and the raw DME pre-heater 12 to further condense to a temperature of about 40° C., and then entered the gas-liquid separator 7 to conduct a gas-liquid separation at an operation pressure of 1.0 MPa (gauge) to obtain a liquid phase and a gas phase. The gas phase included noncondensable gas such as H2, CO, CH4 and CO2, and saturated DME and methanol vapors. 14 kg/h of the gas phase material entered the absorbing column 8, and DME in the gas phase was absorbed with a 200 kg/h methanol-water mixed liquid from the DME rectification column bottom. The absorbed liquid was sent back to the gas-liquid separator 7. About 6 kg/h of the tail gas after absorption was depressurized and vented to a torch tower.

The liquid phase raw DME from the gas-liquid separator 7 was pumped into the DME rectification column 9 to rectify. The ratio of the top reflux quantity and the produced quantity at 18 was 3, and the DME product produced at 18 was at 12630 kg/h with a DME content of ≥99.9%. The noncondensable gas, and DME and methanol vapors from the DME column top returned at 85 kg/h to the absorbing column 8 to conduct the absorption. The reboiler of the DME rectification column 9 required 1.1 MPa (gauge) steam to supply a heat of 1812 KW.

The bottom liquid of the DME rectification column 9 was an aqueous methanol solution with a methanol content of about 40%, 200 kg/h of which was used as the absorbing liquid to the absorbing column 8, and the remaining 10624 kg/h of which was sent to the methanol recovery column 10. 3765 kg/h of the methanol material 19 (containing 5 kg/h of water) was recovered from the column top for recycle use. 6859 kg/h of the process waste water leaving the methanol recovery column, after cooling in a water-cooler, was sent to the waste water treatment system.

The DME rectification column was a plate column. It was operated under a pressure of 1.1 MPa at a column top temperature of 50° C. and a column bottom temperature of 160° C. It had a theoretical plate number of 30. The inlet was at the 11$^{th}$ plate counted from the column top. The outlet for DME was at the 1$^{st}$ plate counted from the column top. The DME rectification column was provided with a condenser at the column top. The column top mass reflux ratio was 3:1.

The methanol recovery column was a plate column. It was operated under a pressure of 0.2 MPa at a column top temperature of 75° C. and a bottom column temperature of 114° C. The methanol recovery column had a theoretical plate number of 30. The inlet was at the 11$^{th}$ plate counted from the column top. The outlet for methanol vapor was at the 1$^{st}$ plate counted from the column top. The methanol recovery column was provided with a condenser at the column top. The column top mass reflux ratio was 3:1.

The absorbing column was a packed column. It was operated under a pressure of 1.0 MPa. It was operated at a temperature of 40° C. It had a theoretical plate number of 6. The inlet was in the middle-lower part of the column.

Example 7

The process chart of the DME production process is shown in FIG. 2.

The DME production scale was 1,000,000 tons/year. The pressure in the fluidized bed reactor was 0.8 MPa (gauge). The methanol feedstock was an industrial methanol with a purity of 90%.

The methanol feedstock at 13 was at 232600 kg/h, wherein the fresh methanol was at 175670 kg/h, water was at 19330 kg/h and the recycled methanol was at 37600 kg/h. The methanol vaporizer 6 had a heat load of 47740 KW and was operated at a temperature of 158° C. under a pressure of 1.5 MPa (gauge). The saturated methanol vapor was sent to the heat-exchanger 5 to be superheated to 200° C. and then to the fluidized bed reactor.

The saturated methanol liquid from the bottom of the methanol vaporizer 6 was sent to the heat-collecting tube of the interior heat collector or the exterior heat collector at a rate of 500000 kg/h to generate a 1.5 MPa methanol vapor at a rate of 45000 kg/h with the methanol vaporization latent heat. The methanol vapor and the saturated methanol liquid returned to the methanol vaporizer, and removed a methanol dehydration reaction heat of about 15000 KW from the reactor. The reaction temperature could be controlled in a range of 250-280° C.

The methanol dehydration reaction product was obtained at the outlet of the fluidized bed reactor 2: 126176 kg/h of DME vapor, 37600 kg/h of methanol vapor, 68714 kg/h of steam and 110 kg/h of noncondensable gas. The reaction product having a temperature of 280° C. entered the heat-exchanger 5 and the methanol pre-heater 11 to heat-exchange with the fed methanol vapor and the methanol feedstock to reach 240° C. and 148° C. respectively, further condensed to a temperature of about 40° C., and then entered the gas-liquid separator 7 to conduct a gas-liquid separation at an operation pressure of 1.1 MPa (gauge) to obtain a liquid phase and a gas phase. The gas phase included noncondensable gas such as H2, CO, CH4 and CO2, and saturated DME and methanol vapors. 136 kg/h of the gas phase material entered the absorbing column 8, and DME in the gas phase was absorbed with a 1500 kg/h methanol-water mixed liquid from the DME rectification column bottom. The absorbed liquid was sent back to the gas-liquid separator 7. About 59 kg/h of the tail gas after absorption was depressurized and vented to a torch tower.

The liquid phase raw DME from the gas-liquid separator 7 was pumped into the DME rectification column 9 to rectify. The ratio of the top reflux quantity and the produced quantity at 18 was 2.5, and the DME product produced at 18 was at 126255 kg/h with a DME content of ≥99.9%. The noncondensable gas, and DME and methanol vapors from the DME column top returned at 845 kg/h to the absorbing column 8 to conduct the absorption. The reboiler of the DME rectification column 9 required 1.1 MPa (gauge) steam to supply a heat of 35820 KW.

The bottom liquid of the DME rectification column 9 was an aqueous methanol solution with a methanol content of about 35%, 1500 kg/h of which was used as the absorbing liquid to the absorbing column 8, and the remaining 106286 kg/h of which was sent to the methanol recovery column 10. 37620 kg/h of the methanol material 19 (containing 20 kg/h of water) was recovered from the column top for recycle use. 68666 kg/h of the process waste water leaving the methanol recovery column, after cooling in a water-cooler, was sent to the waste water treatment system.

The DME rectification column was a plate column. It was operated under a pressure of 1.1 MPa at a column top temperature of 50° C. and a column bottom temperature of 158°

C. It had a theoretical plate number of 35. The inlet was at the 10$^{th}$ plate counted from the column top. The outlet for DME was at the 1$^{st}$ plate counted from the column top. The DME rectification column was provided with a condenser at the column top. The column top mass reflux ratio was 2.5:1.

The methanol recovery column was a plate column. It was operated under a pressure of 0.2 MPa at a column top temperature of 75° C. and a bottom column temperature of 114° C. The methanol recovery column had a theoretical plate number of 35. The inlet was at the 10$^{th}$ plate counted from the column top. The outlet for methanol vapor was at the 1$^{st}$ plate counted from the column top. The methanol recovery column was provided with a condenser at the column top. The column top mass reflux ratio was 1.8:1.

The absorbing column was a packed column. It was operated under a pressure of 1.0 MPa. It was operated at a temperature of 40° C. It had a theoretical plate number of 6. The inlet was in the middle-lower part of the column.

Example 8

The process chart of the DME production process is shown in FIG. 3.

The DME production scale was 1,000,000 tons/year. The pressure in the fluidized bed reactor was 1.2 MPa (gauge). The methanol feedstock was an industrial methanol with a purity of 90%.

The operation conditions were substantially same as those in Example 7. The methanol dehydration reaction product was obtained at the outlet of the fluidized bed reactor 2: 126176 kg/h of DME vapor, 37600 kg/h of methanol vapor, 68714 kg/h of steam and 110 kg/h of noncondensable gas. The reaction product having a temperature of 280° C. entered the heat-exchanger 5 and the methanol pre-heater 11 to heat-exchange with the fed methanol vapor and the methanol feedstock to reach 240° C. and 148° C. respectively and then directly entered the DME rectification column 9 in a gas-liquid two-phase form to rectify. The ratio of the top reflux quantity and the produced quantity at 18 was 3.6, and the DME product produced at 18 was at 126210 kg/h with a DME content of ≥99.9%. The noncondensable gas, and DME and methanol vapors from the DME column top returned at 1839 kg/h to the absorbing column 8 to conduct the absorption. DME in the gas phase was absorbed with a 2500 kg/h aqueous methanol solution from the DME rectification column bottom. The absorbed liquid was sent back to the DME rectification column 9. About 72 kg/h of the tail gas after absorption was depressurized and vented to a torch tower. The reboiler of the DME rectification column 9 required 1.1 MPa (gauge) steam to supply a heat of 18810 KW.

The bottom liquid of the DME rectification column 9 was an aqueous methanol solution with a methanol content of about 35%, 2500 kg/h of which was used as the absorbing liquid to the absorbing column 8, and the remaining 106303 kg/h of which was sent to the methanol recovery column 10. 37640 kg/h of the methanol material 19 (containing 50 kg/h of water) was recovered from the column top for recycle use. 68663 kg/h of the process waste water leaving the methanol recovery column, after cooling in a water-cooler, was sent to the waste water treatment system.

The DME rectification column was a plate column. It was operated under a pressure of 1.1 MPa at a column top temperature of 50° C. and a column bottom temperature of 160° C. It had a theoretical plate number of 35. The inlet was at the 11$^{th}$ plate counted from the column top. The outlet for DME was at the 1$^{st}$ plate counted from the column top. The DME rectification column was provided with a condenser at the column top. The column top mass reflux ratio was 3.6:1.

The methanol recovery column was a plate column. It was operated under a pressure of 0.2 MPa at a column top temperature of 75° C. and a bottom column temperature of 114° C. The methanol recovery column had a theoretical plate number of 35. The inlet was at the 11$^{th}$ plate counted from the column top. The outlet for methanol vapor was at the 1$^{st}$ plate counted from the column top. The methanol recovery column was provided with a condenser at the column top. The column top mass reflux ratio was 1.8:1.

The absorbing column was a packed column. It was operated under a pressure of 1.0 MPa. It was operated at a temperature of 40° C. It had a theoretical plate number of 6. The inlet was in the middle-lower part of the column.

Comparative Examples 1-3

Comparative Examples 1-3 were conducted in a similar manner as Examples 5-7 except that the interior heat collector or the exterior heat collector of the reactor removed heat by the saturated water evaporation. The results of Comparative Examples 1-3 were that the heat loads on the methanol vaporizers were 2800 kw, 6905 kw and 62740 kw respectively. With the manner of removing the reaction heat with the methanol vaporization heat, the energy consumption on the vaporizer 6 for the methanol feedstock can be reduced by about 20-30% according to the method of the present invention. In addition, the relative costs such as that for providing with the saturated steam drum can be dispensed with. These effects were remarkable.

Comparative Examples 4-6

Comparative Examples 4-6 were conducted in a similar manner as Examples 5-7 except that the absorbing column 8 used the methanol feedstock as the absorbing liquid. The results of the Comparative Examples 4-6 were that the required methanol feedstock flows were 850, 920 and 8500 kg/h respectively, and the emitted noncondensable gas still contained about 10-20% of the methanol gas. In addition, if using waste water from the methanol recovery column bottom as the absorbing liquid, the required methanol feedstock flows were 100, 120, 1120 kg/h. With the aqueous methanol solution from the DME rectification column bottom or waste water from the methanol recovery column bottom as the absorbing liquid, the absorbing liquid flows decreased by 7-8 times. The investment for the absorbing column device would be saved. The emitted noncondensable gas barely contained methanol and DME gases.

What is claimed is:

1. A method of producing dimethyl ether from methanol, which comprises the following steps of:
   a methanol feedstock is sent to a catalyst-fluidizable reactor and contacted with the catalyst to conduct a dehydration reaction to produce a dehydrated reaction stream; and said dehydrated reaction stream is passed to a gas-solid separator to separate from the catalyst and obtain a carbon-deposited catalyst and a dehydrated reaction product,
   wherein, a portion or all of said carbon-deposited catalyst is sent to a regenerator to burn the coke for regeneration in a continuous or intermittent manner; and a regenerated catalyst is sent back to the reactor and contacted with the methanol feedstock to react,
   wherein, said dehydrated reaction product is sent to a separation device comprising an absorbing column and a DME rectification column, and optionally a methanol recovery column; a product stream consisting mainly of DME is obtained in the upper part of the DME rectification column; a noncondensable gas entrained with DME and/or methanol is obtained on the top of the DME rectification column; said noncondensable gas is sent to the absorbing column to absorb the entrained DME and/or methanol with an absorbing liquid; the DME rectification column bottom liquid consists substantially of unconverted methanol and water; the DME rectification column bottom liquid is optionally separated by the methanol recovery column to obtain methanol in the upper part of the methanol recovery column and waste water at the methanol recovery column bottom, and wherein the absorbing liquid used in the absorbing column is the DME rectification column bottom liquid and/or waste water from the methanol recovery column bottom.

2. The method of claim 1, wherein the methanol feedstock has a methanol content of 5-100 wt %.

3. The method of claim 1, wherein the catalyst contains Y-zeolite and optionally other molecular sieve but does not contain inorganic oxide(s) and clay.

4. The method of claim 1, wherein said catalyst contains inorganic oxide(s), clay, Y-zeolite, and optionally other molecular sieve.

5. The method of claim 3 or 4, wherein said other molecular sieve is one or more selected from meso porous zeolites, Beta-zeolites, and SAPO-molecular sieves.

6. The method of claim 3 or 4, wherein the weight ratio of other molecular sieve to Y-zeolite is 0-10.

7. The method of claim 3 or 4, wherein said Y-zeolite is selected from the group consisting of Y, HY, REY, REHY, USY, REUSY and mixtures thereof.

8. The method of claim 5, wherein said meso porous zeolite includes ZRP series, ZSP series, ZSM series zeolites and their derivative or modified zeolites.

9. The method of claim 3 or 4, wherein said inorganic oxide is selected from the group consisting of alumina, silica, amorphous silica-alumina and mixtures thereof; and the clay is kaolin and/or halloysite.

10. The method of claim 1, wherein the dehydration reaction is conducted at a temperature of 100-550° C., under a pressure of 1~1000 kPa, with a weight ratio of the catalyst to the methanol feedstock of 0.001-50, at a weight hourly space velocity of 0.01-100⁻.

11. The method of claim 1, wherein the proportion of the carbon-deposited catalyst subjected to coke-burning is 0.5-100% by the total weight of the carbon-deposited catalyst.

12. The method of claim 1 or 11, wherein when a portion of the carbon-deposited catalyst enters the regenerator for the coke-burning regeneration, the remaining carbon-deposited catalyst returns to the reactor, and said portion of the carbon-deposited catalyst subjected to coke-burning comprises 0.5-99% by the total weight of the carbon-deposited catalyst.

13. The method of claim 1, wherein the regeneration is one-stage regeneration or two-stage regeneration, and said regenerated catalyst is a partially regenerated catalyst and/or a full regenerated catalyst.

14. The method of claim 3 or 4, wherein said catalyst containing Y-zeolite is selected from the group consisting of a fresh catalyst, a regenerated catalyst, a half-regenerated catalyst, a catalyst to be regenerated, and a combination thereof.

15. The method of claim 1, wherein the catalyst-fluidizable reactor is selected from the group consisting of a fluidized bed, a riser, a descending transfer line reactor, a composite reactor of riser and fluidized bed, a composite reactor of riser and descending transfer line, a composite reactor of two or more risers, a composite reactor of two or more fluidized beds, and a composite reactor of two or more descending transfer lines, each of the above reactors may be divided into two or more reaction zones.

16. The method of claim 1, wherein the regenerated catalyst is cooled to 100-650° C. in a direct or indirect heat-exchange manner, and then sent back to the reactor.

17. The method of claim 16, wherein the direct heat-exchange is to directly contact the regenerated catalyst with air or steam having a lower temperature for heat-exchange, and the direct heat-exchanger is embodied in a fluidized bed or a riser; wherein the indirect heat-exchange is to use a heat exchanger, through the shell of which the hot catalyst passes and through the tube of which the saturated water or other heat-exchanging medium passes.

18. The method of claim 1, wherein the methanol feedstock is in a liquid phase form or in a gas phase form.

19. The method of claim 1, wherein the methanol feedstock is indirectly heat-exchanged with the reaction stream and the catalyst in the reactor and/or the catalyst in the regenerator before being fed to the catalyst-fluidizable reactor and contacted with the catalyst.

20. The method of claim 1, wherein the separation device comprises an absorbing column, a DME rectification column, and a methanol recovery column, wherein 99.9-90 vol % of the DME rectification column bottom liquid is sent into the methanol recovery column, and 0.1-10 vol % of the DME rectification column bottom liquid is sent into the absorbing column as the absorbing liquid.

21. The method of claim 1, wherein the separation device further comprises a gas-liquid separator, wherein the dehydrated reaction product and/or the absorbing column bottom liquid is sent to the gas-liquid separator; after the gas-liquid separation, a liquid phase portion and a gas phase portion are obtained, wherein the liquid phase portion is sent to the DME rectification column, and the gas phase portion is sent to the absorbing column.

22. The method of claim 1, wherein the DME rectification column is a packed column or a plate column; wherein the methanol recovery column is a packed column or a plate column; and the absorbing column is a packed column or a plate column.

23. The method of claim 22, wherein the DME rectification column is operated under a pressure of 0.1-1.5 MPa, at a column top temperature of 20-90° C. and a column bottom temperature of 100-220° C.; wherein the DME rectification column has a theoretical plate number of 10-35, the inlet is at a position between the $4^{th}$ plate and the $16^{th}$ plate counted from the column top, and the outlet for DME is at a position between the $1^{st}$ plate and the $5^{th}$ plate counted from the column top.

24. The method of claim 22, wherein the methanol recovery column is operated under a pressure of 0.01-0.6 MPa, at a column top temperature of 65-170° C. and a bottom column temperature of 100-220° C.; wherein the methanol recovery column has a theoretical plate number of 10-35, the inlet is at a position between the $4^{th}$ plate and the $16^{th}$ plate counted from the column top, and the outlet for methanol vapor is at a position between the $1^{st}$ plate and the $5^{th}$ plate counted from the column top.

25. The method of claim 22, wherein the absorbing column is operated under a pressure of 0.1-1.5 MPa, at a temperature of 30-70° C., wherein the absorbing column has a theoretical plate number of 1-15, and the inlet is in the middle-lower part of the column.

* * * * *